(12) United States Patent
Nakamoto et al.

(10) Patent No.: US 10,947,195 B2
(45) Date of Patent: Mar. 16, 2021

(54) PRODUCTION METHOD FOR DIHYDROXYINDOLES

(71) Applicant: Kao Corporation, Tokyo (JP)

(72) Inventors: Masayoshi Nakamoto, Wakayama (JP); Norihiro Ito, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/761,142

(22) PCT Filed: Oct. 31, 2018

(86) PCT No.: PCT/JP2018/040458
§ 371 (c)(1),
(2) Date: May 1, 2020

(87) PCT Pub. No.: WO2019/088152
PCT Pub. Date: May 9, 2019

(65) Prior Publication Data
US 2020/0270208 A1    Aug. 27, 2020

(30) Foreign Application Priority Data
Nov. 1, 2017 (JP) .............................. JP2017-212038

(51) Int. Cl.
*C07D 209/08* (2006.01)
(52) U.S. Cl.
CPC .................. *C07D 209/08* (2013.01)
(58) Field of Classification Search
CPC .................................................. C07D 209/08
See application file for complete search history.

(56) References Cited

U.S. PATENT DOCUMENTS

| 5,704,949 A | 1/1998 | Prota et al. | |
| 2012/0177588 A1* | 7/2012 | Desmurs | C07D 209/42 424/62 |

OTHER PUBLICATIONS

"The Chemical Society of Japan, 4th Experimental Chemistry Lecture 1: Basic Operation I, Maruzen Inc.", Nov. 5, 1990, pp. 180-181 and 189-194, total 19 pages.
"The Chemical Society of Japan, New experimental chemistry lecture 1: Basic operation I, Maruzen Inc.", Mar. 20, 1978, p. 293-295, total 10 pages.
Charkoudian et al., "Fe (III)-Coordination Properties of Neuromelanin Components: 5,6-Dihydroxyindole and 5,6-Dihydroxyindole-2-carboxylic Acid", Inorganic Chemistry, 2006, vol. 45, No. 9, pp. 3657-3664.
Edge et al., "Dopaquinone redox exchange with dihydroxyindole and dihydroxyindole carboxylic acid", Pigment Cell Res., 2006, vol. 19, pp. 443-450.
International Search Report, issued in PCT/JP2018/040458, PCT/ISA/210, dated Jan. 22, 2019.
Tran et al., "Chemical and Structural Disorder in Eumelanins: A Possible Explanation for Broadband Absorbance", Biophysical Journal, Feb. 2006, vol. 90, No. 3, pp. 743-752.
Wakamatsu et al., "Preparation of Eumelanin-Related Metabolites 5, 6-Dihydroxyindole, 5,6-Dihydroxyindole-2-carboxylic Acid, and Their O-Methyl Derivatives", Analytical Biochemistry, 1988, vol. 170, p. 335-340.
English translation of the International Preliminary Report on Patentability and Written Opinion of the International Searching Authority, dated May 14, 2020, for International Application No. PCT/JP2018/040458.

* cited by examiner

*Primary Examiner* — Shawquia Jackson
(74) *Attorney, Agent, or Firm* — Birch, Stewart, Kolasch & Birch, LLP.

(57) ABSTRACT

A method for producing dihydroxyindoles includes: a step 1 of obtaining an aqueous first solution including dihydroxyindoles obtained by causing at least a material selected from the group consisting of 3-(3,4-dihydroxyphenyl)alanine and a derivative of 3-(3,4-dihydroxyphenyl)alanine to react with an oxidizing agent; and a step 2 of obtaining an oleaginous second solution in which the dihydroxyindoles are extracted in an extraction solvent by mixing the first solution obtained in the step 1 with the extraction solvent. Before the first solution obtained in the step 1 is mixed with the extraction solvent in the step 2, a water-insoluble by-product is removed from the first solution.

16 Claims, 9 Drawing Sheets

PRODUCTION METHOD FOR DIHYDROXYINDOLES

TECHNICAL FIELD

The present invention relates to a method for producing dihydroxyindoles.

BACKGROUND ART

Melanin is a yellow to black pigment formed in animals and plants, and is known to have an ultraviolet absorption function, a radical trapping function, an antioxidation function, and other functions. Melanin is a safe material of a biological origin, and thus, has been widely used for cosmetics, food products, plastic products, and other products. For example, melanin is used as an ultraviolet absorber in, for example, sunscreens and sunglasses, is used as an antioxidant in, for example, food and plastic products, and is used as a pigment in, for example, a hair die.

In a living body, 3-(3,4-dihydroxyphenyl)alanine (DOPA) as a substrate compound is oxidized by catalysis of tyrosinase as a melanogenesis enzyme to generate a dihydroxyindoles (e.g., 5,6-dihydroxyindole and 5,6-dihydroxyindole-2-carboxylic acid) as a melanin precursor through dopaquinone. These dihydroxyindoles are polymerized to biosynthesize melanin. The thus biosynthesized melanin is a stable macromolecular compound that is present in the form of small particles in melanin-producing cells, such as skin and hair, is insoluble in water and an organic solvent, and is not dissolved without using hot concentrated sulfuric acid or strong alkali. Thus, in the case of using melanin as a dye for fibers, leather, and the like, for example, even when melanin is used as an additive without any treatment, melanin, which is insoluble in water and an organic solvent, cannot be used for dyeing by immersion in tissues of a dyeing object. In view of this, water-soluble dihydroxyindoles are used as an additive to form melanin in a dyeing object.

As a method for producing dihydroxyindoles for use in such an application, Patent Document 1, for example, discloses a method with which hexacyanoferrate(III) is added to an aqueous solution containing 3-(3,4-dihydroxyphenyl)alanine for reaction so that dihydroxyindoles are produced, and a complex of hexacyanoferrate (II) is removed from an aqueous solution containing the obtained dihydroxyindoles. Non-patent Documents 1 and 2 disclose methods with which hexacyanoferrate(III) is added to an aqueous solution containing 3-(3,4-dihydroxyphenyl)alanine for reaction so that dihydroxyindoles are produced, and an aqueous solution containing the obtained dihydroxyindoles is supplemented with an extraction solvent of ethyl acetate to thereby extract dihydroxyindoles.

CITATION LIST

Patent Document

Patent Document 1: U.S. Pat. No. 5,704,949

Non-Patent Document

Non-Patent Document 1: Wakamatsu, K. and Ito, S. (1988) Analytical Biochemistry 170, 335-340

Non-Patent Document 2: R. Edge, M. d'lschia, E. J. Land, A. Napolitano, S. Navaratham, L. Panzella, A. Pezzella, C. A. Ramsden and P. A. Riley (2006) Pigment Cell Res.19; 443-450

SUMMARY OF THE INVENTION

The present invention relates to a method including: a step 1 of obtaining an aqueous first solution including dihydroxyindoles by causing at least a material selected from the group consisting of 3-(3,4-dihydroxyphenyl)alanine and a derivative of 3-(3,4-dihydroxyphenyl)alanine to react with an oxidizing agent; and a step 2 of obtaining an oleaginous second solution in which the dihydroxyindoles are extracted in an extraction solvent by mixing the first solution obtained in the step 1 with the extraction solvent, wherein before the first solution obtained in the step 1 is mixed with the extraction solvent in the step 2, a water-insoluble by-product is removed from the first solution.

BRIEF DESCRIPTION OF THE DRAWINGS

FIG. 2A A view illustrating an apparatus configuration for performing circulating filtration FIG. 2B A view illustrating an apparatus configuration for performing one-pass filtration FIG. 3 A view illustrating a configuration of a filter including a single filter medium FIG. 4A A view illustrating a configuration of a filter including a plurality of filter media arranged in series FIG. 4B A view illustrating a configuration of a filter including a plurality of filter media arranged in parallel FIG. 4C A view illustrating a configuration of a filter including a plurality of filter media arranged in parallel and in series FIG. 5A A first illustration of a refining process FIG. 5B second illustration of the refining process FIG. 6A A first illustration of a solvent replacement process FIG. 6B A second illustration of the solvent replacement process FIG. 6C A third illustration of the solvent replacement process

DESCRIPTION OF EMBODIMENTS

An embodiment will be described in detail below.

A method for producing dihydroxyindoles according to an embodiment includes a reaction process (step 1), a refining process (step 2), and a solvent replacement process (step 3) as an optional process. In this specification, 3-(3,4-dihydroxyphenyl)alanine will be abbreviated as DOPA, one or more materials selected from the group consisting of 3-(3,4-dihydroxyphenyl)alanine and a derivative thereof will be abbreviated as DOPAs, 5,6-dihydroxyindole will be abbreviated as DHI, and dihydroxyindoles will be abbreviated as DHIs.

<Reaction Process (Step 1)>

In a reaction process, DOPAs and an oxidizing agent are caused to react with each other so that DHIs are produced, thereby obtaining an aqueous first solution L1 including DHIs. At this time, it is suitable to mix a DOPAs solution D of a DOPAs aqueous solution or an aqueous suspension with an oxidizing agent solution O of an oxidizing agent aqueous solution or an aqueous suspension. The reaction between DOPAs and the oxidizing agent is an oxidation-reduction reaction.

Figure 1:
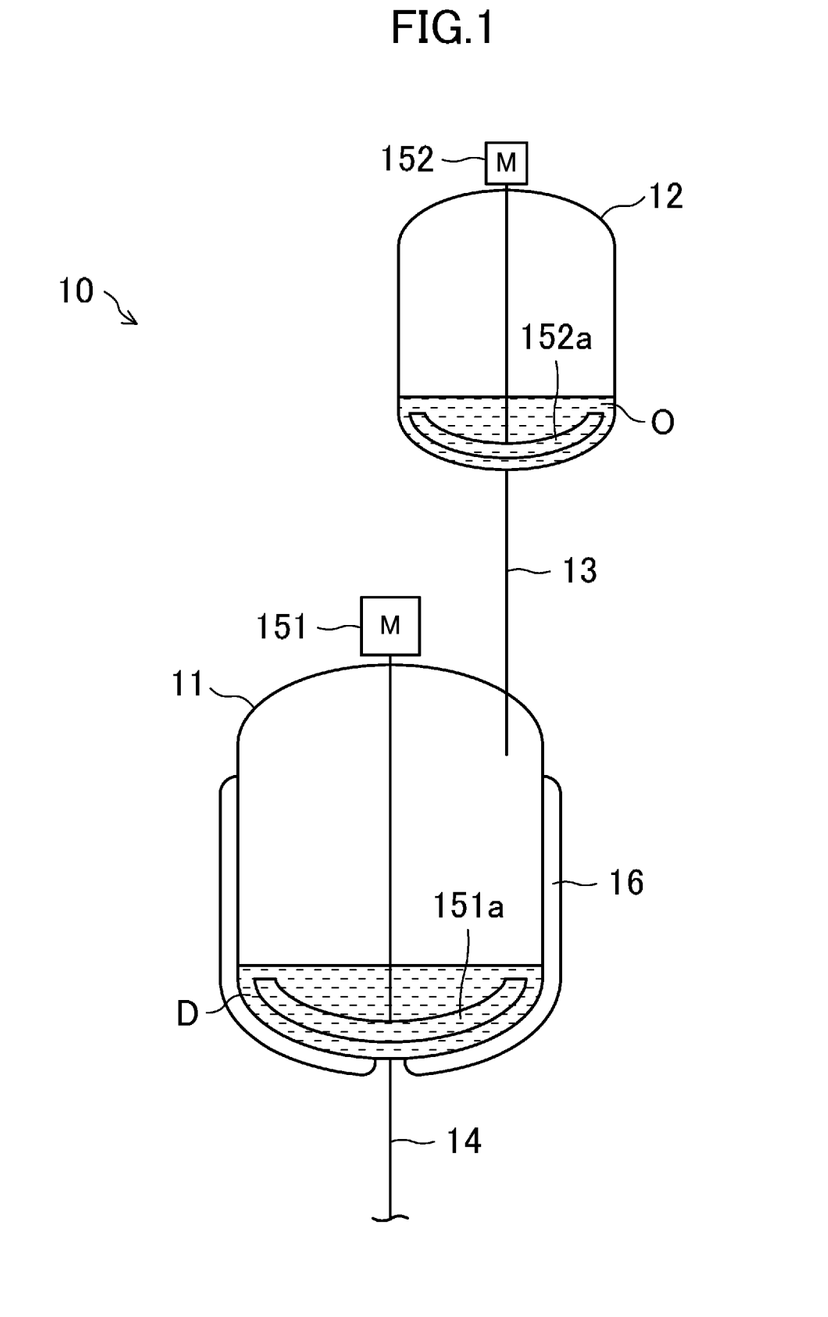
FIG. 1 A view illustrating a configuration of a reaction apparatus

FIG. 1 illustrates an example of a reaction apparatus 10 used in the reaction process (step 1).

The reaction apparatus 10 includes a reaction tank 11 and an oxidizing agent tank 12. An oxidizing agent supply pipe 13 extending from the bottom of the oxidizing agent tank 12 is introduced into an upper portion of the reaction tank 11. A discharge pipe 14 extends from the bottom of the reaction tank 11. The reaction tank 11 and the oxidizing agent tank 12 are provided with agitators 151 and 152, respectively. Agitating impellers 151a and 152a of the agitators 151 and 152 only need to sufficiently agitate a low-viscosity solution, and may be, for example, paddle impellers, disc turbines, tilt paddle impellers, or anchor impellers. The reaction tank 11 is provided with a jacket 16 for adjusting the temperature in the tank.

Specifically, first, water is poured into the reaction tank 11. Water is suitably ion-exchanged water or distilled water, for example. It is suitable to use water whose dissolved oxygen concentration has been reduced by supplying an inert gas such as a nitrogen gas or an argon gas. The dissolved oxygen concentration of water is suitably 1.0 mg/L or less, and more suitably 0.5 mg/L or less. The dissolved oxygen concentration of this water is measured with a commercially available dissolved oxygen meter (the same hereinafter).

In the reaction tank 11, before or after pouring water, the oxygen concentration is suitably reduced by supplying an inert gas such as a nitrogen gas or an argon gas. The oxygen concentration of a gaseous phase in the reaction tank 11 is suitably 1.0% by volume or less, and more suitably 0% by volume. The oxygen concentration of the gaseous phase in the reaction tank 11 is measured with a commercially available oxygen concentration meter (the same hereinafter). The supply of the inert gas to the gaseous phase in the reaction tank 11 is suitably continuously performed during an operation in this reaction process.

Next, while water is agitated by starting the agitator 151 disposed in the reaction tank 11, DOPAs are supplied to be dissolved or dispersed, thereby obtaining a DOPAs solution D. This method for preparing the DOPAs solution D is a suitable specific example, and may be a method in which DOPAs are first supplied in the reaction tank 11 and then water is supplied to the reaction tank 11, a method in which water and DOPAs are supplied to the reaction tank 11 at the same time, or a method in which each of water and DOPAs is divided into parts and these parts are alternately supplied to the reaction tank 11.

Examples of a DOPA among DOPAs include D-DOPA (3,4-dihydroxy-D-phenylalanine) and L-DOPA (3,4-dihydroxy-L-phenylalanine). Examples of a DOPA derivative among DOPAs include 2-3',4'-dihydroxyphenyl ethylamine derivatives (e.g., N-octanoyl-4-(2-aminoethyObenzene-1,2-diol and N-octanoyl-4,2-(3,4-dihydropheny)ethylamine), 4-(2-aminoethyl)benzene-1,2-diol(dopamine), salt of D-DOPA (e.g., potassium salt and sodium salt), salt of L-DOPA (e.g., potassium salt and sodium salt), lower (carbon number of 1 to 4) alkyl ester of DOPA, α-lower (carbon number of 1 or more and 4 or less) alkyl DOPA, and isomers thereof. The DOPAs solution D may contain a chemical substance that is inactive to DOPAs such as benzoates, as well as DOPAs.

The content of DOPAs in the DOPAs solution D is suitably 0.10% by mass or more, more suitably 0.20% by mass or more, and much more suitably 0.30% by mass or more, from the viewpoint of obtaining high productivity, and is suitably 1.0% by mass or less, more suitably 0.70% by mass or less, and much more suitably 0.50% by mass or less, from the viewpoint of enhancing the yield of DHIs while suppressing progress of a side reaction. The content of DOPAs in the DOPAs solution D is suitably 0.10% by mass or more and 1.0% by mass or less, more suitably 0.20% by mass or more and 0.70% by mass or less, and much more suitably 0.30% by mass or more and 0.50% by mass or less.

In addition, water is poured into the oxidizing agent tank 12. Water is suitably ion-exchanged water or distilled water, for example. It is suitable to use water whose dissolved oxygen concentration has been reduced by supplying an inert gas such as a nitrogen gas or an argon gas. The dissolved oxygen concentration of water is suitably 1.0 mg/L or less, and more suitably 0.5 mg/L or less.

Thereafter, while water is agitated by starting the agitator 152 disposed in the oxidizing agent tank 12, an oxidizing agent is placed and dissolved or dispersed, thereby obtaining an oxidizing agent solution O. This preparation method for the oxidizing agent solution O is a suitable specific example. Alternatively, the oxidizing agent may be first supplied in the oxidizing agent tank 12 with water then being supplied to the oxidizing agent tank 12, or water and the oxidizing agent may be supplied to the oxidizing agent tank 12 at the same time or alternately, or each of water and DOPAs may be divided into parts so that these parts water and DOPAs are alternately supplied to the oxidizing agent tank 12.

Examples of the oxidizing agent include: alkali metal salts of hexacyanoferrate(III) acid such as potassium hexacyanoferrate(III), sodium hexacyanoferrate(III), and lithium hexacyanoferrate(III); hexacyanoferrate(III); metal oxide such as manganese dioxide, silver oxide, palladium dioxide, and potassium permanganate; and metal salts such as iron chloride, vanadium(V) trichloride oxide, and ceric sulfate (IV). As the oxidizing agent, one or more of these materials are suitably used. From the viewpoint of productivity, hexacyanoferrate(III) is suitably used, and an alkali metal salt of hexacyanoferrate(III) acid is more suitably used. From the viewpoint of versatility, potassium hexacyanoferrate(III) is more suitably used. In the presence of a metal catalyst such as copper, manganese, or nickel, oxygen can be used as an oxidizing agent.

In the case of using hexacyanoferrate(III) such as an alkali metal salt of hexacyanoferrate(III) acid as the oxidizing agent, the content of hexacyanoferrate(III) such as an alkali metal salt of hexacyanoferrate(III) acid of the oxidizing agent in the oxidizing agent solution O with respect to the mole number of DOPAs in the DOPAs solution D is suitably 2.0 equivalents or more, more suitably 2.6 equivalents or more, and much more suitably 3.5 equivalents or more, from the viewpoint of enhancing the yield of DHIs while promoting a reaction, and is suitably 6.0 equivalents or less, more suitably 5.5 equivalents or less, and much more suitably 4.6 equivalents or less, from the viewpoint of enhancing the yield of DHIs while suppressing progress of a side reaction. The content of hexacyanoferrate(III) such as an alkali metal salt of hexacyanoferrate(III) acid of the oxidizing agent in the oxidizing agent solution O with respect to the mole number of DOPAs in the DOPAs solution D is suitably 2.0 equivalents or more and 6.0 equivalents or less, more suitably 2.6 equivalents or more and 5.5 equivalents or less, and much more suitably 3.5 equivalents or more and 4.6 equivalents or less.

The oxidizing agent solution O suitably includes a base agent, from the viewpoint of promoting a reaction while maintaining the pH during the reaction at a weak basicity. Examples of the base agent include alkali metal salt of hydrogencarbonate ions, such as potassium hydrogencarbonate and sodium hydrogencarbonate, and alkali metal salt of carbonate ions, such as potassium carbonate and sodium carbonate. As the base agent, one or more of these materials are suitably used. The oxidizing agent solution O may additionally include a chemical substance that is inactive to the oxidizing agent such as benzoates.

From the viewpoint of promoting a reaction by maintaining the pH during the reaction at a moderate weak basicity, the content of the base agent in the oxidizing agent solution O with respect to the mole number of DOPAs in the DOPAs solution D is suitably 3.9 equivalents or more, more suitably 5.1 equivalents or more, and much more suitably 5.9 equivalents or more, and from a similar viewpoint, is suitably 9.0 equivalents or less, more suitably 7.8 equivalents or less, and much more suitably 6.3 equivalents or less The content of the base agent in the oxidizing agent solution O with respect to the mole number of DOPAs in the DOPAs solution D is suitably 3.9 equivalents or more and 9.0 equivalents or less, more suitably 5.1 equivalents or more and 7.8 equivalents or less, and much more suitably 5.9 equivalents or more and 6.3 equivalents or less.

Subsequently, while the DOPAs solution D is agitated with the agitator 151 in the reaction tank 11, the oxidizing agent solution O is dropped into the DOPAs solution D in the reaction tank 11 from the oxidizing agent tank 12 through the oxidizing agent supply pipe 13.

From the viewpoint of application possibility to mass production, the time of dropping of the oxidizing agent solution O is suitably one minute or more, more suitably 3 minutes or more, and much more suitably 5 minutes or more, and from the viewpoint of enhancing the yield of DHIs while suppressing progress of a side reaction, is suitably one hour or less, more suitably 30 minutes or less, and much more suitably 10 minutes or less. The time of dropping of the oxidizing agent solution O is suitably one minute or more and one hour or less, more suitably 3 minutes or more and 30 minutes or less, and much more suitably 5 minutes or more and 10 minutes or less.

Then, by the dropping of the oxidizing agent solution O into the DOPAs solution D, the oxidation-reduction reaction between DOPAs and hexacyanoferrate(III) is caused to progress to thereby produce DHIs. Although the oxidizing agent solution O from the oxidizing agent tank 12 is added to the DOPAs solution D in the reaction tank 11 in this embodiment, the technique disclosed here is not limited to this example as long as the DOPAs solution D and the oxidizing agent solution O are mixed. For example, the DOPAs solution D may be added to the oxidizing agent solution O or the DOPAs solution D and the oxidizing agent solution O may be supplied to a solution tank at the same time or alternately.

From the viewpoint of reducing the reaction time by increasing the reaction rate, the reaction temperature of DOPAs and the oxidizing agent is suitably 10° C. or more, more suitably 25° C. or more, and much more suitably 30° C. or more, and from the viewpoint of enhancing the yield of DHIs while suppressing progress of a side reaction, is suitably 50° C. or less, more suitably 45° C. or less, and much more suitably 40° C. or less. The reaction temperature of DOPAs and the oxidizing agent is suitably 10° C. or more and 50° C. or less, and more suitably 25° C. or more and 45° C. or less, and much more suitably 30° C. or more and 40° C. or less. This reaction temperature can be controlled by setting a liquid temperature with the jacket 16 disposed on the reaction tank 11, and in preparation of the DOPAs solution D in the reaction tank 11, the liquid temperature of the DOPAs solution D is suitably set at this reaction temperature.

From the viewpoint of enhancing the yield of DHIs, the reaction time (aging time) of DOPAs and the oxidizing agent is suitably 2 hours or more, more suitably 3 hours or more, and much more suitably 4 hours or more, from the start of dropping of the oxidizing agent solution O, and from the viewpoint of enhancing productivity, is suitably 22 hours or less, more suitably 6 hours or less, and much more suitably 5 hours or less. The reaction time of DOPAs and the oxidizing agent is suitably 2 hours or more and 22 hours or less, more suitably 3 hours or more and 6 hours or less, and much more suitably 4 hours or more and 5 hours or less.

The produced DHIs depend on DOPAs as raw materials, and examples of the DHIs include DHI, salt thereof (e.g., potassium salt and sodium salt), 5,6-dihydroxyindole-2-carboxylic acid, and salt thereof (e.g., potassium salt and sodium salt). DHIs suitably include one or more of these materials.

In the manner described above, in the reaction tank 11, the aqueous first solution L1 containing DHIs is obtained.

From the viewpoint of stabilizing DHIs, the obtained first solution L1 is suitably subjected to pH adjustment by adding a pH adjuster. Examples of the pH adjuster include a phosphoric acid aqueous solution, dilute sulfuric acid, and diluted hydrochloric acid. As the pH adjuster, one or more of these materials are suitably used. From the viewpoint of enhancing the yield by stabilizing DHIs, the pH of the first solution L1 after the pH adjustment is suitably 3.0 or more, more suitably 3.3 or more, and much more suitably 3.5 or more, and from the viewpoint of enhancing a filtration rate during filtration described later and obtaining an excellent phase split at extraction, is suitably 5.5 or less, more suitably 5.3 or less, and much more suitably 5.0 or less. The pH of the first solution L1 after the pH adjustment is suitably 3.0 or more and 5.5 or less, more suitably 3.3 or more and 5.3 or less, and much more suitably 3.5 or more and 5.0 or less.

In the method for producing DHIs according to this embodiment, before the first solution L1 obtained in this reaction process is mixed with an extraction solvent in a next refining process, a water-insoluble by-product is removed from the first solution L1. The "water-insoluble by-product" herein is a by-product of the oxidation-reduction reaction between DOPAs and the oxidizing agent, and refers to a by-product whose solubility at 20° C. is 1 mg/100 g-$H_2O$ or less. Examples of the water-insoluble by-product include melanin and an intermediate thereof.

In the technique disclosed in Patent Document 1, a complex of hexacyanoferrate (II) is removed from a reaction solution containing DHIs. The reaction solution, however, contains other impurities such as unreacted materials. Thus, from the viewpoint of enhancing purity of DHIs, dihydroxyindoles are suitably extracted in an extraction solvent to be separated as disclosed in Non-patent Documents 1 and 2. For such extraction of DHIs using the extraction solvent, it has been required to enhance the extraction yield.

On the other hand, the inventors found that a mixture of an extraction solvent with the first solution L1 including a water-insoluble by-product causes powder emulsion of a water-insoluble by-product near the interface between the first solution L1 and the extraction solvent to unintentionally form a third phase so that phase separation between the first solution L1 and the second solution L2 is hindered. The inventors also found that formation of this third phase is a cause of a decrease in the extraction yield of DHIs. To solve this problem, phases of the first solution L1 and the extraction solvent are appropriately separated by removing the water-insoluble by-product from the first solution L1 so that the yield of extracting DHIs in the extraction solvent can be enhanced, and the phase separation can be more quickly performed. In view of this, in the method for producing DHIs according to this embodiment, the water-insoluble by-product is removed as described above before the aqueous first solution L1 produced by generating DHIs in the reaction process is mixed with an extraction solvent in a next refining process. Accordingly, the extraction yield of DHIs by using the extraction solvent in the next refining process can be enhanced. The "extraction yield" herein refers to a percentage of the molar quantity of DHIs included in the extraction solvent collected after extraction separation with respect to the molar quantity of DHIs generated by the reaction.

Examples of the removal operation of the water-insoluble by-product include filtration and centrifugal separation. Among these operations, the removal operation of the water-insoluble by-product is suitably filtration, from the viewpoint of convenience of the operation.

Figure 2A:
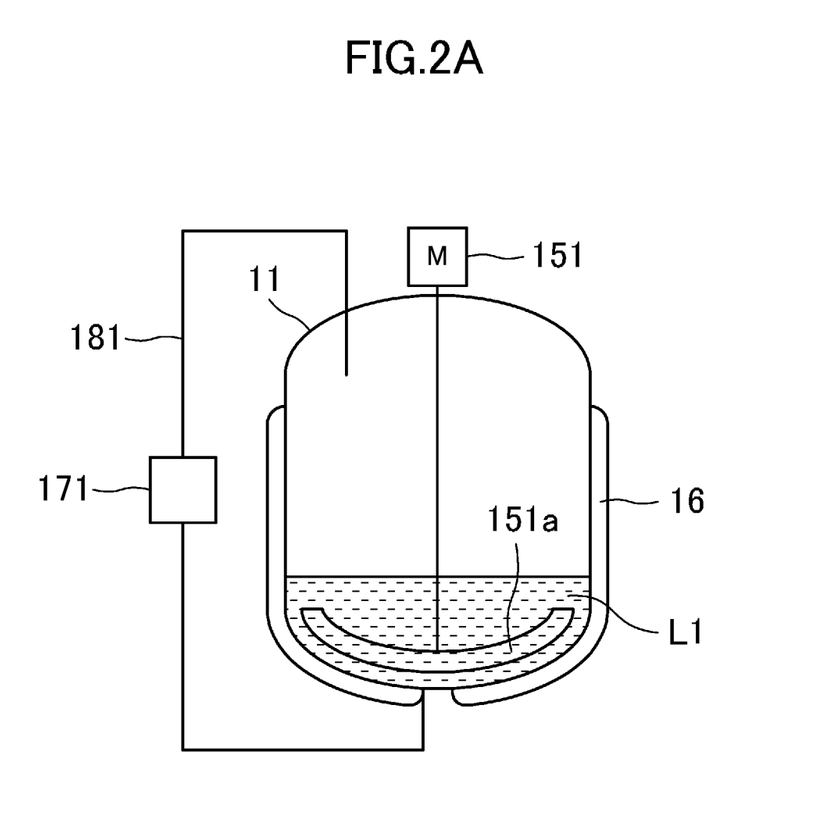
Figure 2B:
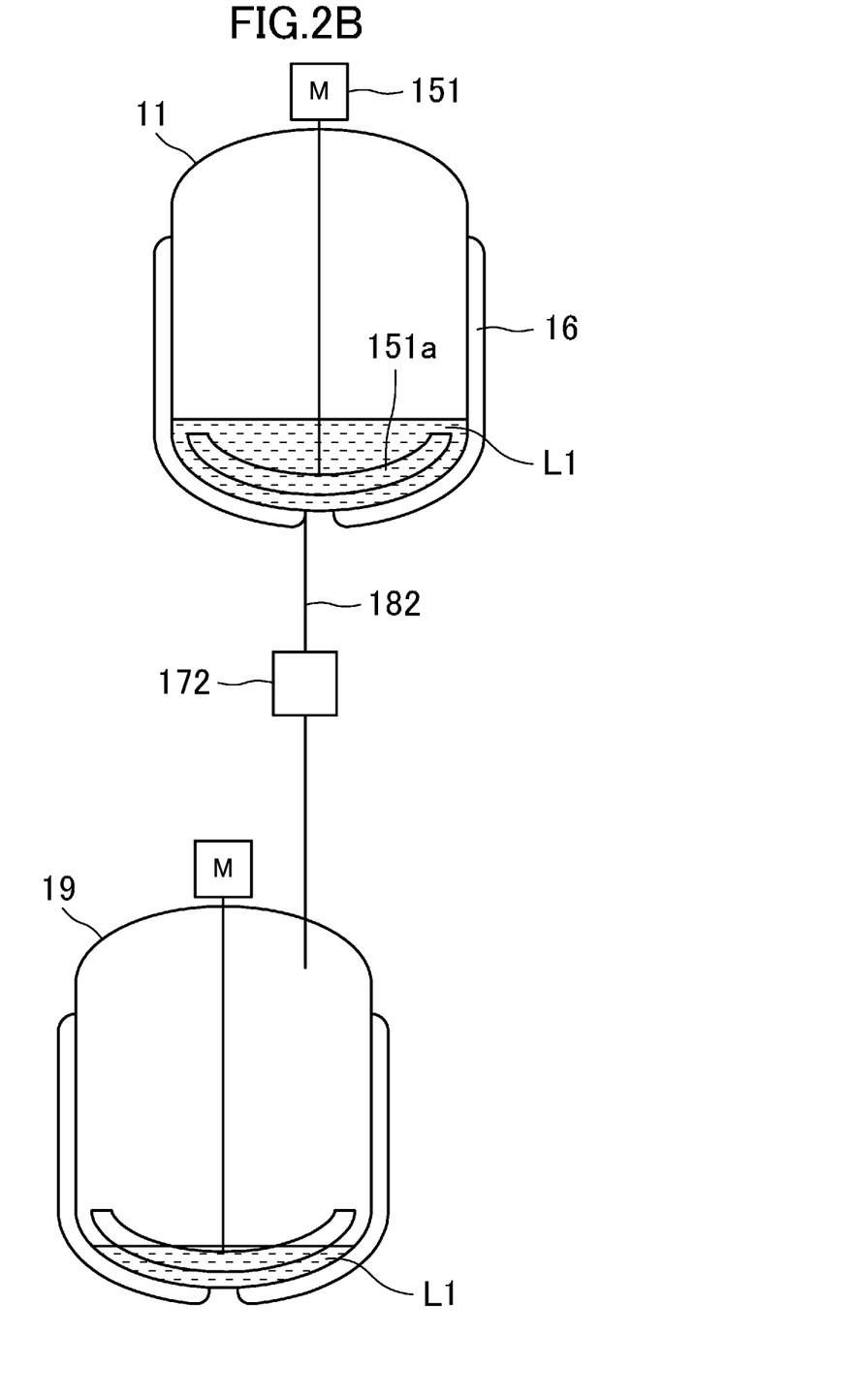

The method for removing the water-insoluble by-product from the first solution L1 through filtration is not limited to a specific method, and may be, for example, a method in which a circulation pipe 181 provided with a filter 171 is disposed in the reaction tank 11 in which the first solution L1 is caused to circulate for circulating filtration, and the first solution L1, which is a filtrate after the filtration, is stored in the reaction tank 11 as illustrated in FIG. 2A. The number of passes for the first solution L1 in the circulation pipe 181 is calculated by dividing, by the volume of the first solution L1 in the reaction tank 11, the total circulation liquid amount obtained by multiplying the flow rate of the first solution L1 in the circulation pipe 181 by a circulation time. From the viewpoint of enhancing the extraction yield by removing the water-insoluble by-product, the number of passes is suitably twice or more, more suitably three times or more, and much more suitably four times or more, and from the viewpoint of reducing a filtration process time and enhancing productivity, is suitably 10 times or less, more suitably eight times or less, much more suitably six times or less. As illustrated in FIG. 2B, the above method may be a method in which an inter-tank coupling pipe 182 extending from the reaction tank 11 is provided with a filter 172, and is connected to a filtrate tank 19 in which the first solution L1 is distributed and subjected to one-pass filtration so that the first solution L1 as a filtrate of the filtration is stored in the filtrate tank 19.

Figure 3:
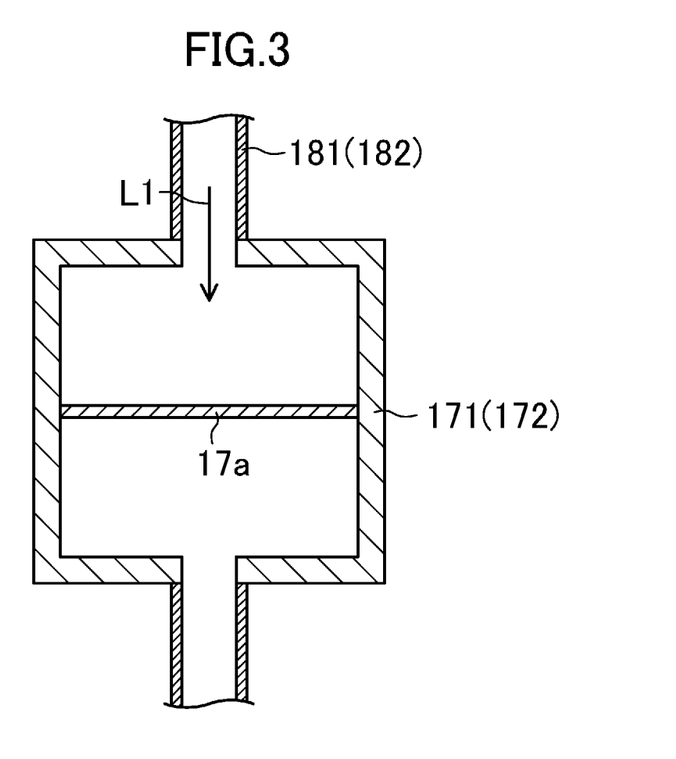
Figure 4A:
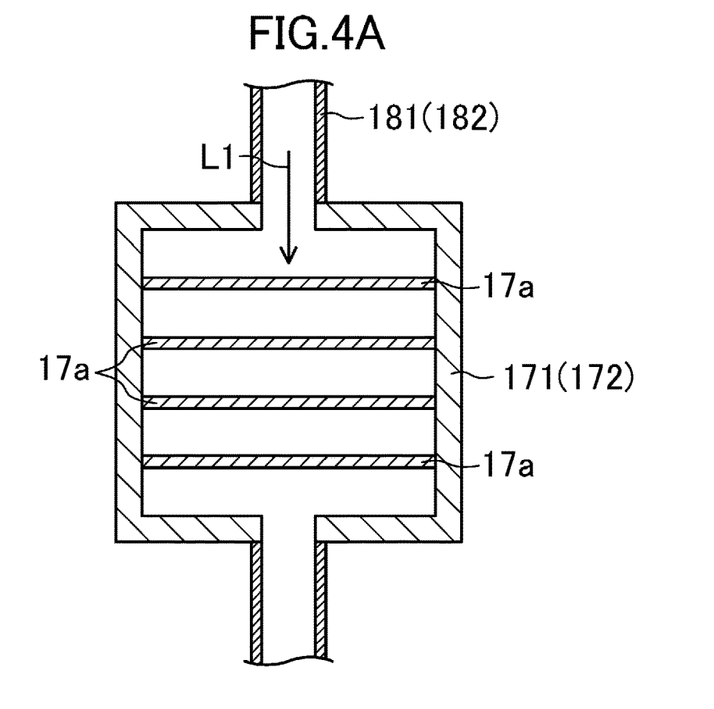
Figure 4B:
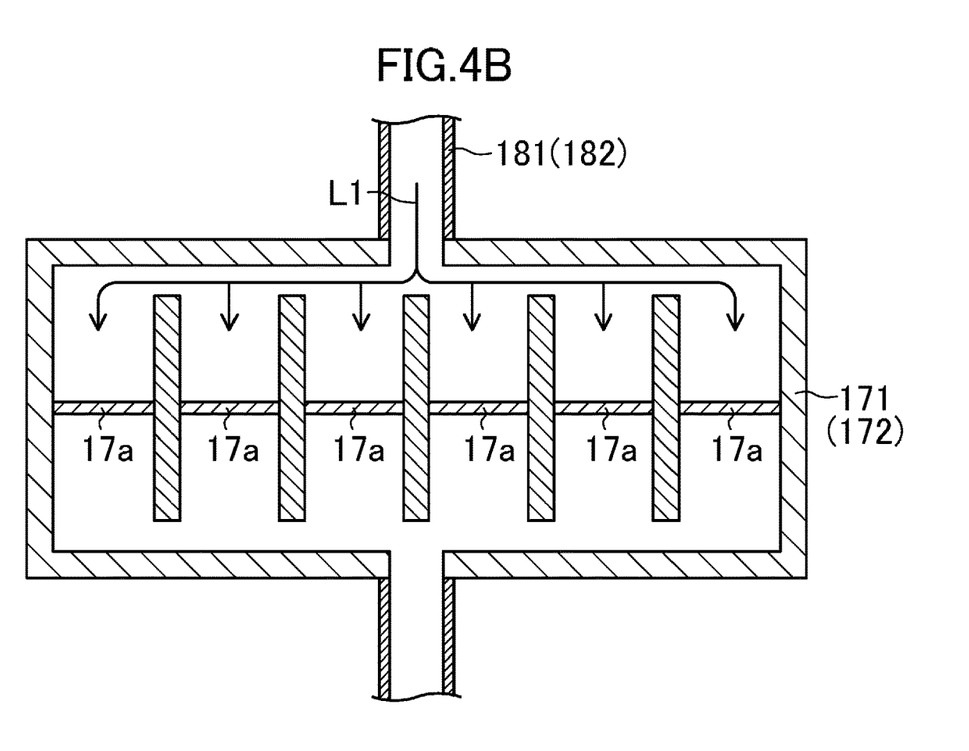
Figure 4C:
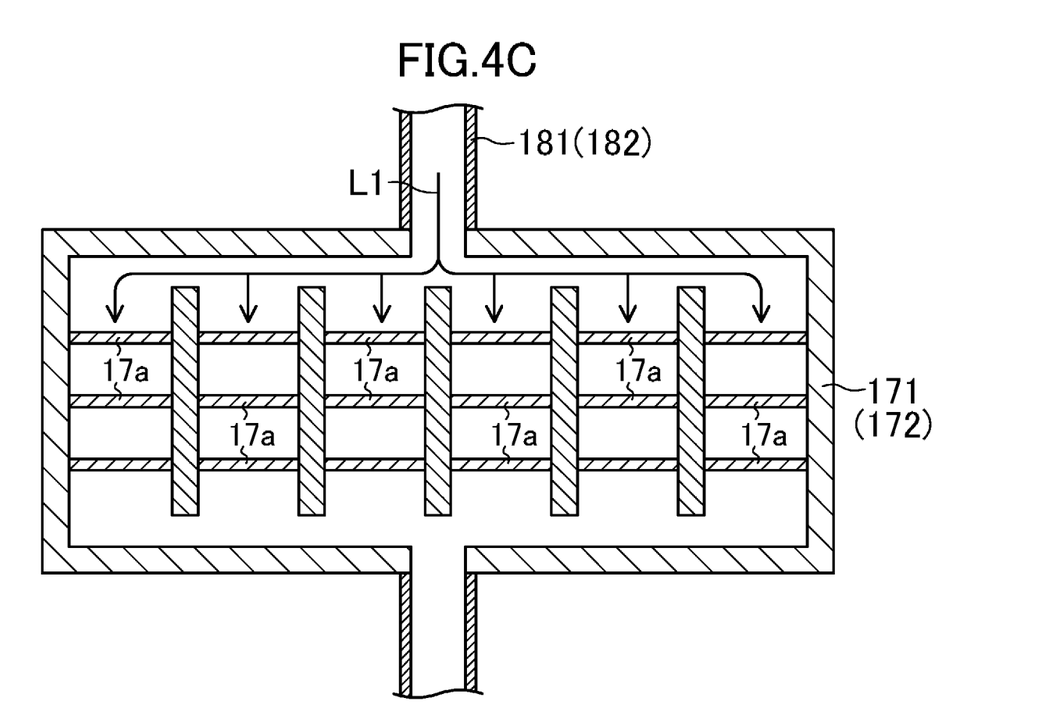

As illustrated in FIG. 3, each of the filters 171 and 172 may include a single filter medium 17a, or may include a plurality of filter media 17a. In the case where each of the filters 171 and 172 includes the plurality of filter media 17a, the plurality of filter media 17a may be arranged in series along the flow direction of the first solution L1 as illustrated in FIG. 4A. The plurality of filter media 17a arranged in series may be spaced apart from each other. The plurality of filter media 17a arranged in series may have the same aperture or may have different apertures. In the latter case, in the plurality of filter media 17a arranged in series, the filter medium 17a having a large aperture is suitably located at an upstream side with the filter medium 17a having a smaller aperture located at a downstream side. More suitably, the apertures may decrease stepwise from the upstream side to the downstream side. As illustrated in FIG. 4B, the plurality of filter media 17a may be arranged in parallel such that parts of the first solution L1 branched in the filters 171 and 172 pass through the individual filter media 17a. The plurality of filter media 17a arranged in parallel suitably have the same aperture. The configurations of the plurality of filter media 17a illustrated in FIGS. 4A and 4B may be combined. Specifically, as illustrated in FIG. 4C, the plurality of filter media 17a may be arranged in such a manner that the plurality of filter media 17a are arranged in parallel so that parts of the first solution L1 branched in the filters 171 and 172 pass through the individual filter media 17a and parts of the plurality of filter media 17a corresponding to each of the divided parts of the first solution L1 are arranged in series along the flow direction of the first solution L1.

From the viewpoint of increasing the filtration rate, the aperture of each filter medium 17a disposed in the filters 171 and 172 is suitably 0.1 µm or more, more suitably 0.5 µm or more, and much more suitably 1.0 µm or more, and from the viewpoint of enhancing the extraction yield of DHIs in the extraction solvent by removing water-insoluble by-product, is suitably 5.0 µm or less, more suitably 2.0 µm or less, and much more suitably 1.5 µm or less. The aperture of each filter medium 17a disposed in the filters 171 and 172 is 0.1 µm or more and 5.0 µm or less, more suitably 0.5 µm or more and 2.0 µm or less, and much more suitably 1.0 µm or more and 1.5 µm or less.

From the viewpoint of removing water-insoluble by-product, the filter medium 17a is not limited to a specific material. From the viewpoint of increasing the filtration rate, the filter medium 17a is suitably made of a hydrophilic material.

<Refining Process (Step 2)>

In the refining process (step 2), the first solution L1 obtained in the reaction process (step 1) is mixed with an extraction solvent so that DHIs are extracted in the extraction solvent, thereby obtaining an oleaginous second solution L2.

Figure 5A:
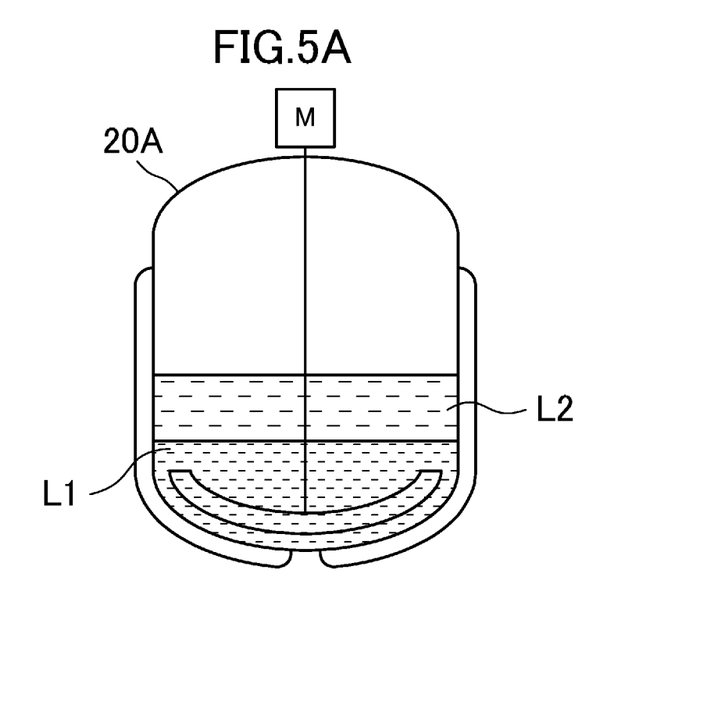
Figure 5B:
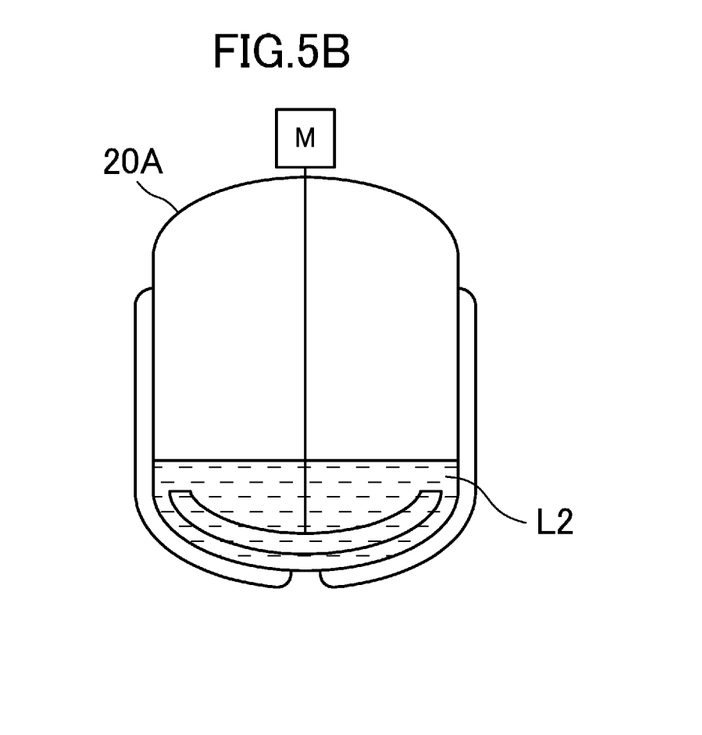

As a specific example, as illustrated in FIG. 5A, in a tank A 20A in which the first solution L1 obtained in the reaction process is stored, an extraction solvent is added while the first solution L1 is agitated so that DHIs are extracted in the extraction solvent, and at this time, the solution is separated in phase into: a lower layer of a water-phase first solution L1 in which cyanide remains; and an upper layer of an oil-phase second solution L2 in which DHIs are extracted in the extraction solvent and then, as illustrated in FIG. 5B, the lower layer of the first solution L1 is discharged from the bottom of the tank A 20A, thereby obtaining the oleaginous second solution L2. Here, the tank A 20A may be the reaction tank 11 used in the reaction process and illustrated in FIGS. 1, 2A, and 2B, may be the filtrate tank 19 illustrated in FIG. 2B, or may be another solution tank to which the first solution L1 is then transferred. Although the extraction solvent is added to the first solution L1 in the configuration of this embodiment, in the case of transferring the first solution L1 from the reaction tank 11, the technique disclosed here is not limited to this configuration as long as the first solution L1 is mixed with the extraction solvent. For example, the first solution L1 may be added to the extraction solvent, or the first solution L1 and the extraction solvent may be added to the solution tank at the same time or alternately.

In the tank A 20A, the oxygen concentration is suitably reduced by supplying an inert gas such as a nitrogen gas or an argon gas. The oxygen concentration of the gaseous phase in the tank A 20A is suitably 1.0% by volume or less, and more suitably 0% by volume. The supply of the inert gas to the gaseous phase in the tank A 20A is suitably continuously performed during an operation of this refining process.

From the viewpoint of layer separation, the extraction solvent is suitably an organic solvent having an octanol/water distribution coefficient (LogP) of 0 (zero) or more and 4.0 or less. Examples of the extraction solvent include ethyl acetate (0.73) and diethyl ether (0.89) that are organic solvents each having an octanol/water distribution coefficient less than 0.90, methyl isobutyl ketone (1.4), dichloromethane (1.3), and cyclohexane (3.4) that are organic solvents each having an octanol/water distribution coefficient larger than 0.90 (values in parentheses are octanol/water distribution coefficients). As the extraction solvent, one or more of these materials are suitably used, and from the viewpoint of enhancing extraction efficiency, it is suitable for the extraction solvent to include an organic solvent having an octanol/water distribution coefficient of 1.5 or less, and more suitably less than 0.90, and it is much more suitable for the extraction solvent to include ethyl acetate. A chemical substance that is inactive to DHIs such as benzoates and phosphates may be added to the first solution L1, as well as the extraction solvent.

From the viewpoint of enhancing the yield of extracting DHIs in the extraction solvent, the mixture amount of the extraction solvent in the first solution L1 with respect to the volume of the first solution L1 at the end of the reaction is suitably 20% by volume or more, more suitably 30% by volume or more, and much more suitably 50% by volume, and from the viewpoint of reducing manufacturing costs by reducing the waste liquid amount, is suitably 400% by volume or less, more suitably 200% by volume or less, and much more suitably 100% by volume or less. The mixture amount of the extraction solvent in the first solution L1 is suitably 20% by volume or more and 400% by volume or less, more suitably 30% by volume or more and 200% by volume or less, and much more suitably 50% by volume or more and 100% by volume or less, with respect to the volume of the first solution L1 at the end of the reaction.

From the viewpoint of enhancing the yield of extracting DHIs in the extraction solvent, it is suitable to agitate a mixed solution of the first solution L1 and the extraction solvent after or at the same time as addition of the extraction solvent to the first solution L1.

In the case of agitating the mixed solution after the addition of the extraction solvent, from the viewpoint of enhancing the yield of extracting DHIs in the extraction solvent, the agitation time (extraction time) of the mixed solution is suitably 10 minutes or more, more suitably 15 minutes or more, and much more suitably 20 minutes or more, and from the viewpoint of enhancing productivity, is suitably 120 minutes or less, more suitably 90 minutes or less, and much more suitably 60 minutes or less. The agitation time (extraction time) of the mixed solution is suitably 10 minutes or more and 120 minutes or less, more suitably 15 minutes or more and 90 minutes or less, and much more suitably 20 minutes or more and 60 minutes or less.

In the case of agitating the first solution L1 while adding the extraction solvent, from the viewpoint of enhancing the yield of extracting DHIs in the extraction solvent, the agitation time (extraction time) of the first solution L1 from the start of addition of the extraction solvent is suitably 10 minutes or more, more suitably 15 minutes or more, and much more suitably 20 minutes or more, and from the viewpoint of enhancing productivity, is suitably 120 minutes or less, more suitably 90 minutes or less, and much more suitably 60 minutes or less. The agitation time (extraction time) of the first solution L1 is suitably 10 minutes or more and 120 minutes or less, more suitably 15 minutes or more and 90 minutes or less, and much more suitably 20 minutes or more and 60 minutes or less.

After mixing of the extraction solvent, from the viewpoint of removing impurities, the oleaginous second solution L2 is suitably set apart from an aqueous solution, and from the viewpoint of further removing impurities, the obtained second solution L2 is then suitably cleaned with wash water.

The cleaning method may be a method in which in the tank A 20A storing the obtained second solution L2, wash water is brought into sufficient contact with the second solution L2 by adding wash water while agitating the second solution L2, and then, the lower-layer water phase out of the upper-layer oil phase of the second solution L2 and the lower-layer water phase subjected to phase separation is discharged from the bottom of the tank A 20A.

From the viewpoint of maintaining the pH of wash water around neutral with stability, the amount of addition of wash water to the second solution L2 is suitably 10% by volume or more, more suitably 20% by volume or more, and much more suitably 30% by volume or more, and from the viewpoint of enhancing the yield of DHIs, is suitably 100% by volume or less, more suitably 80% by volume or less, and much more suitably 50% by volume or less. The amount of addition of wash water to the second solution L2 with respect to the volume of the second solution L2 is suitably 10% by volume or more and 100% by volume or less, more suitably 20% by volume or more and 80% by volume or less, and much more suitably 30% by volume or more and 50% by volume or less.

From the viewpoint of maintaining the pH of wash water around neutral with stability, the cleaning time of the second solution L2 with wash water is suitably 30 minutes or more, more suitably 45 minutes or more, and much more suitably 60 minutes or more, and from the viewpoint of enhancing the yield of DHIs, is suitably 120 minutes or less, more suitably 105 minutes or less, and much more suitably 90 minutes or less. The cleaning time of the second solution L2 with wash water is suitably 30 minutes or more and 120 minutes or less, more suitably 45 minutes or more and 105 minutes or less, and much more suitably 60 minutes or more and 90 minutes or less.

From the viewpoint of maintaining the pH around neutral, wash water may contain polybasic acid salt. Examples of the polybasic acid salt include potassium salt of phosphoric acid, potassium salt of citric acid, potassium salt of carbonic acid, sodium salt of phosphoric acid, sodium salt of citric acid, and sodium salt of carbonic acid. As the polybasic acid, one or more of these materials is suitably used, and more suitably, the polybasic acid includes potassium salt of phosphoric acid (dipotassium hydrogen phosphate and dipotassium hydrogen phosphate).

The yield of extracting DHIs in the extraction solvent is suitably 25 mol % or more, more suitably 50 mol % or more, and much more suitably 75 mol %.

<Solvent Replacement Process (Step 3)>

In the solvent replacement process (step 3) as an optional process, it is suitable that the second solution L2 obtained in the refining process (step 2) is mixed with water W and an extraction solvent is evaporated to thereby perform solvent displacement, thereby obtaining a DHIs solution of an aqueous solution or an aqueous dispersion containing DHIs as an aqueous third solution L3. From the viewpoint of efficiency in production, concentration adjustment is suitably performed together with the solvent displacement.

Figure 6A:
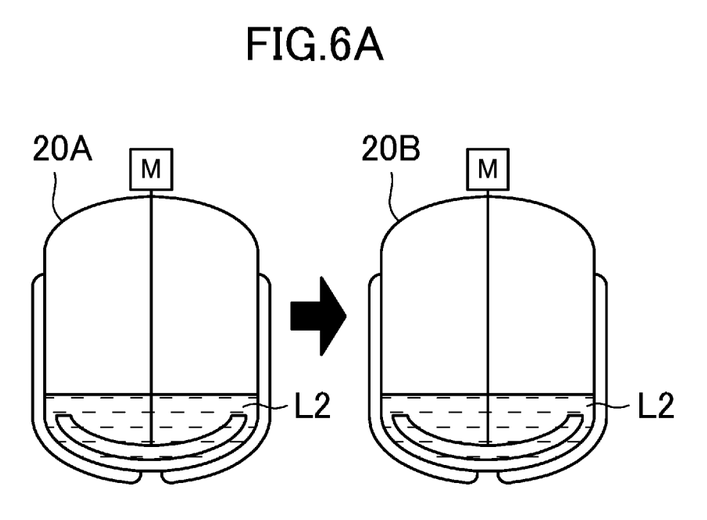

From the viewpoint of enhancing purity of the DHIs solution, the solvent replacement process is suitably performed in the tank B 20B whose inside has been cleaned. In view of this, first, as illustrated in FIG. 6A, the second solution L2 obtained in the refining process is discharged from the tank A 20A and transferred, and then, is supplied to and stored in the tank B 20B whose inside is cleaned. The tank B 20B may be a solution tank different from the tank A 20A, and may be the original tank A 20A whose inside has been cleaned after discharge of the second solution L2.

In the tank B 20B whose inside has been cleaned, the oxygen concentration is suitably reduced by supplying an inert gas such as a nitrogen gas or an argon gas. The oxygen concentration of the gaseous phase in the tank B 20B is suitably 1.0% by volume or less and more suitably 0% by volume. The supply of the inert gas to the gaseous phase in the tank B 20B is suitably continuously performed during an operation of this solvent replacement process.

Figure 6B:
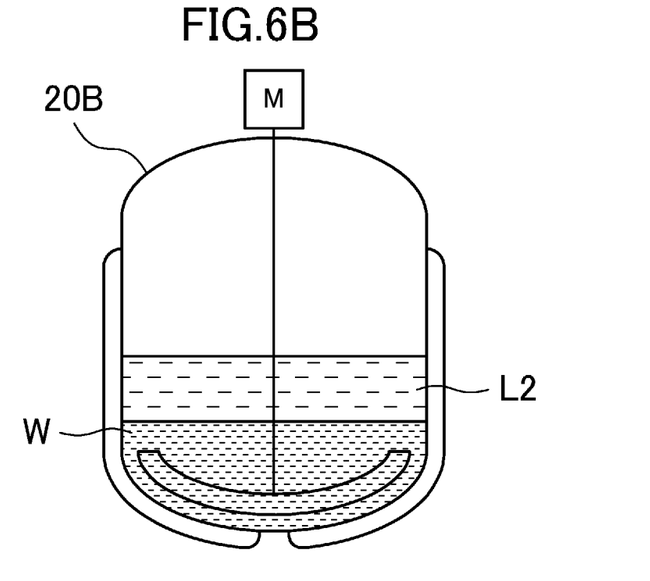

Subsequently, as illustrated in FIG. 6B, water W is added to the second solution L2 in the tank B 20B, and then, the second solution L2 to which water W is added is heated in the tank B 20B so that an extraction solvent is evaporated and the extraction solvent is displaced by water W by solvent displacement. From the viewpoint of reducing the concentration of an organic solvent, this solvent displacement by addition of water W and evaporation of the extraction solvent is suitably performed a plurality of times. The number of solvent displacements is suitably two or more and four or less.

Water W to be added is suitably ion-exchanged water or distilled water, for example. Water W is suitably water whose dissolved oxygen concentration has been reduced by supplying an inert gas such as a nitrogen gas or an argon gas. The dissolved oxygen concentration of water W is suitably 1.0 mg/L or less and more suitably 0.5 mg/L or less.

First addition of water W to the second solution L2 at the first solvent displacement may be performed on the second solution L2 suppled to the tank B 20B, or may be performed on the second solution L2 that has been discharged from the tank A 20A and has not yet been supplied to the tank B 20B. Addition of water W at the second and subsequent solvent displacements is performed on liquid remaining in the tank B 20B.

From the viewpoint of efficiently performing solvent displacement, the amount of addition of water W with respect to the volume of the second solution L2 in the first solvent displacement or with respect to the volume of the liquid remaining in the tank B 20B in the second and subsequent solvent displacements, is suitably 50% by volume or more, more suitably 80% by volume or more, and much more suitably 100% by volume or more, and from a similar viewpoint, is suitably 150% by volume or less, more suitably 120% by volume or less, and much more suitably 110% by volume or less. The amount of addition of water W with respect to the volume of the second solution L2 in the first solvent displacement or the volume of liquid remaining in the tank B 20B in the second and subsequent solvent displacements, is suitably 50% by volume or more and 150% by volume or less, more suitably 80% by volume or more and 120% by volume or less, and much more suitably 100% by volume or more and 110% by volume or less.

From the viewpoint of increasing an evaporation rate of the extraction solvent, the liquid temperature in evaporating the extraction solvent is suitably 40° C. or more, more suitably 50° C. or more, and much more suitably 60° C. or more, and from the viewpoint of suppressing thermal decomposition of DHIs, is suitably 90° C. or less, more suitably 85° C. or less, and much more suitably 80° C. or less. The liquid temperature in evaporating the extraction solvent is suitably 40° C. or more and 90° C. or less, more suitably 50° C. or more and 85° C. or less, and much more suitably 60° C. or more and 80° C. or less. Steam of the evaporated extraction solvent is suitably condensed by, for example, a heat exchanger, and collected.

From the viewpoint of increasing an evaporation rate of the extraction solvent, the pressure in evaporating the extraction solvent in the first solvent displacement is suitably an atmospheric pressure (101.325 kPa (abs)) or less, more suitably 90 kPa (abs) or less, and much more suitably 80 kPa (abs) or less. From the viewpoint of increasing an evaporation rate of the extraction solvent, the pressure in evaporating the extraction solvent in the second and subsequent solvent displacements is suitably 80 kPa (abs) or less, more suitably 40 kPa (abs) or less, and much more suitably 10 kPa (abs) or less.

Figure 6C:
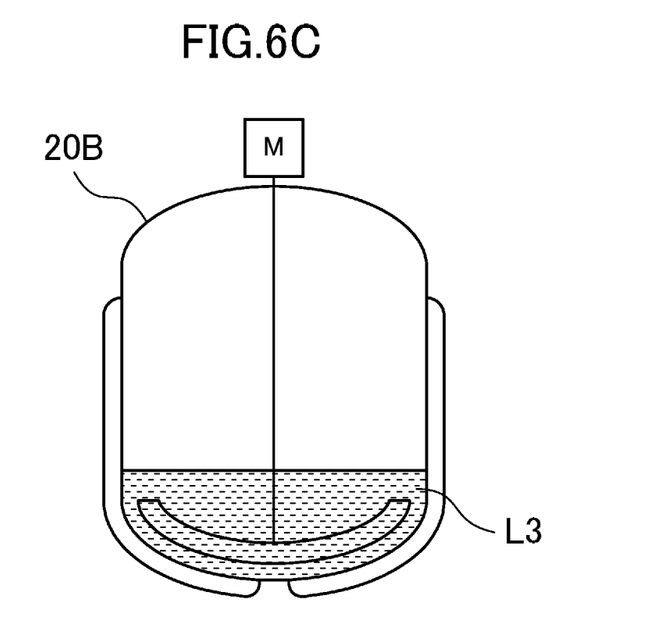

Then, as illustrated in FIG. 6C, water and a water-soluble solvent are added to liquid remaining in the tank B 20B after solvent displacement and the concentration is adjusted so that DHIs can be obtained in the form of a DHIs solution, which is the aqueous third solution L3. Examples of the water-soluble solvent include ethanols.

The content of DHIs in the DHIs solution of the obtained third solution L3 is suitably 0.3% by mass or more, more suitably 0.5% by mass or more, and much more suitably 1.0% by mass or more. The content of DHIs is measured by high performance liquid chromatography (HPLC).

The content of the organic solvent in the DHIs solution of the obtained third solution L3 is suitably 1.5% by mass or less, more suitably 1.0% by mass or less, and much more suitably 0.5% by mass or less. The content of the organic solvent is measured by gas chromatography (GC).

In a case where the DHIs solution of the third solution L3 after solvent displacement is used for dyeing such as hair dyeing, the content of DHIs is suitably about 1% by mass. From this viewpoint, the second solution L2 is suitably condensed before solvent displacement.

The condensation of the second solution L2 may be performed in such a manner that the second solution L2 obtained in the refining process is condensed by evaporating the extraction solvent in the tank A 20A and then the condensed second solution L2 is discharged from the tank A 20A and supplied to and stored in the tank B 20B. Alternatively, the condensation may be performed in such a manner that the second solution L2 obtained in the refining process is discharged from the tank A 20A and is supplied to and stored in the tank B 20B, and then, the second solution L2 is condensed by evaporating the extraction solvent in the tank B 20B. The condensation may also be performed in such a manner that the second solution L2 obtained in the refining process is discharged from the tank A 20A and is supplied to another solution tank and condensed by evaporating the extraction solvent, and then the resulting solution is discharged from the solution tank so that the condensed second solution L2 is supplied to and stored in the tank B 20B.

From the viewpoint of increasing an evaporation rate of the extraction solvent, the liquid temperature in condensing the second solution L2 is suitably 40° C. or more, more suitably 50° C. or more, and much more suitably 60° C. or more, and from the viewpoint of suppressing thermal decomposition of DHIs, is suitably 90° C. or less, more suitably 85° C. or less, and much more suitably 80° C. or less. The liquid temperature in condensing the second solution L2 is suitably 40° C. or more and 90° C. or less, more suitably 50° C. or more and 85° C. or less, and much more suitably 60° C. or more and 80° C. or less.

From the viewpoint of increasing an evaporation rate of the extraction solvent, the pressure in condensing the second solution L2 is suitably an atmospheric pressure (101.325 kPa (abs)) or less, more suitably 100 kPa (abs) or less, and much more suitably 90 kPa (abs) or less.

In regard to the embodiment described above, the following configuration will be described.

<1> A method for producing DHIs includes: a step 1 of obtaining an aqueous first solution including DHIs obtained by causing DOPAs and an oxidizing agent to react with each other; and a step 2 of obtaining an oleaginous second solution in which the DHIs are extracted in an extraction solvent by mixing the first solution obtained in the step 1 with the extraction solvent, and before the first solution obtained in the step 1 is mixed with the extraction solvent in the step 2, a water-insoluble by-product is removed from the first solution.

<2> The method described in <1> in which the water-insoluble by-product is removed by filtration.

<3> The method described in <2> in which the filtration uses a filter medium having an aperture of 5.0 μm or less.

<3-1> The method described in <2> in which the filtration uses a filter medium having an aperture of 2.0 μm or less.

<3-2> The method described in <2> in which the filtration uses a filter medium having an aperture of 1.5 μm or less.

<4> The method described in any one of <2> to <3-2> in which the filtration uses a filter medium having an aperture of 0.1 μm or more.

<4-1> The method described in any one of <2> to <3-2> in which the filtration uses a filter medium having an aperture of 0.5 μm or more.

<4-2> The method described in any one of <2> to <3-2> in which the filtration uses a filter medium having an aperture of 1.0 μm or more.

<5> The method described in any one of <2> to <4-2> in which the filtration is formed by causing the first solution to circulate in a circulation pipe provided with a filter including the filter medium.

<6> The method described in <5> in which the number of circulations of the first solution in the circulation pipe is suitably twice or more, more suitably three times or more, and much more suitably four times or more, and suitably 10 times or less, more suitably eight times or less, and much more suitably six times or less.

<7> The method described in any one of <2> to <4> in which the filtration is performed through one-pass filtration by distributing the first solution in a pipe provided with a filter including the filter medium.

<8> The method described in any one of <5> to <7> in which the filter includes a single filter medium.

<9> The method described in any one of <5> to <7> in which the filter includes a plurality of filter media.

<10> The method described in <9> in which the plurality of filter media are arranged in series along a flow direction of the first solution.

<11> The method described in <10> in which apertures of the plurality of filter media arranged in series decrease in size stepwise from an upstream side to a downstream side.

<12> The method described in any one of <9> to <11> in which the plurality of filter media are arranged in parallel such that parts of the first solution branched in the filter individually pass through the plurality of filter media.

<13> The method described in <12> in which the plurality of filter media arranged in parallel have an identical aperture.

<14> The method described in any one of <1> to <13> in which in the step 1, an aqueous solution or an aqueous suspension including 0.20% by mass or more of the DOPAs is mixed with an aqueous solution or an aqueous suspension of the oxidizing agent.

<15> The method described in <14> in which a content of the DOPAs is suitably 0.30% by mass or more, and suitably 1.0% by mass or less, more suitably 0.70% by mass or less, and much more suitably 0.50% by mass or less.

<16> The method described in <14> or <15> in which the oxidizing agent includes alkali metal salt of hexacyanoferrate(III) acid.

<17> The method described in <16> in which a content of an alkali metal of hexacyanoferrate(III) acid of the oxidizing agent with respect to a mole number of the DOPAs is suitably 2.0 equivalents or more, more suitably 2.6 equivalents or more, and much more suitably 3.5 equivalents or more, and is suitably 6.0 equivalents or less, more suitably 5.5 equivalents or less, and much more suitably 4.6 equivalents or less.

<18> The method described in any one of <14> to <17> in which an aqueous solution or an aqueous suspension of the oxidizing agent includes a base agent.

<19> The method described in <18> in which the base agent includes alkali metal salt of hydrogencarbonate ions.

<20> The method described in <18> or <19> in which a content of the base agent with respect to a mole number of the DOPAs is suitably 3.9 equivalents or more, more suitably 5.1 equivalents or more, and much more suitably 5.9 equivalents or more, and is suitably 9.0 equivalents or less, more suitably 7.8 equivalents or less, much more suitably 6.3 equivalents or less.

<21> The method described in any one of <1> to <20> in which the extraction solvent includes an organic solvent whose octanol/water distribution coefficient is 0 or more and 4.0 or less.

<21-1> The method described in any one of <1> to <20> in which the extraction solvent includes an organic solvent whose octanol/water distribution coefficient is suitably 0 or more and 1.5 or less, and more suitably 0 or more and less than 0.9.

<22> The method described in <21> in which the extraction solvent includes ethyl acetate.

<23> The method described in any one of <1> to <22> in which a mixture amount of the extraction solvent in the first solution with respect to a volume of the first solution at the end of reaction, is suitably 20% by volume or more, more suitably 30% by volume or more, and much more suitably 50% by volume or more, and is suitably 400% by volume or less, more suitably 200% by volume or less, and much more suitably 100% by volume or less.

<24> The method described in any one of <1> to <23> in which an extraction yield of the DHIs in the extraction solvent is suitably 25 mol % or more, more suitably 50 mol % or more, and much more suitably 75 mol % or more.

EXAMPLES (Production of DHI)

Tests for DHI production were conducted according to first through fourth examples and a comparative example. The production was performed under a nitrogen atmosphere. The results of the production are also shown in Table 1.

The content (HPLC) and purity of DHI were measured in the following manner.

DHI Content (HPLC)

First, to a 50 mL of a volumetric flask whose inside has been replaced by nitrogen, 1.0 g of sodium ascorbate as an antioxidant, 2.0 g of a 0.1% by weight phosphate aqueous solution containing 0.2% by weight of potassium benzoate, and 1.0 g of a DHI solution were added and mixed. Next, a 0.1% by weight phosphate aqueous solution was added up to 50 mL to the volumetric flask to adjust the solution, and the resulting solution was measured by HPLC, and the content of DHI was calculated. Each solution was adjusted to have a dissolved oxygen concentration of 1.0 mg/L or less by blowing a nitrogen gas therein.

Method for Measuring Purity

The purity of DHI was calculated as a percentage of a peak area value of DHI with respect to a value obtained by subtracting area values of sodium ascorbate and potassium benzoate from peak area values of all the materials measured by HPLC.

First Example

—Reaction Process (Step 1)—

In a first example, a reaction apparatus including a reaction tank and an oxidizing agent tank similar to those illustrated in FIG. 1 was prepared. In the reaction apparatus, a circulation pipe provided with a filter was disposed in the reaction tank in a manner similar to the configuration illustrated in FIG. 2A. The reaction tank had a capacity of 300 L, and was provided with an agitator including an anchor impeller and a temperature-adjusting jacket. The oxidizing agent tank was provided with an agitator. The filter included a single filter medium having an aperture of 1.2 μm.

First, a nitrogen gas was continuously supplied to the reaction tank, and water whose dissolved oxygen concentration had been adjusted to 1.0 mg/L or less by blowing a nitrogen gas was poured into the reaction tank. While water was agitated in the reaction tank, DOPA was placed and dissolved in the reaction tank, thereby preparing 175 L of a DOPA aqueous solution (DOPAs solution) having a concentration of 0.33% by mass. At this time, hot water was caused to flow in the jacket so that the liquid temperature of the DOPA aqueous solution was adjusted to 35° C.

In addition, water was poured in the oxidizing agent tank. While water was agitated in the oxidizing agent tank, potassium hexacyanoferrate(III) of an oxidizing agent and potassium hydrogencarbonate of a base agent were placed and dissolved in the oxidizing agent tank, thereby preparing 25.2 L of a potassium hexacyanoferrate(III) aqueous solution (oxidizing agent solution) having a concentration of 16.8% by mass. The content of potassium hexacyanoferrate (III) in this potassium hexacyanoferrate(III) aqueous solution was 4.0 equivalents with respect to the mole number of DOPA in the DOPA aqueous solution. The content of potassium hydrogencarbonate of the base agent in the potassium hexacyanoferrate(III) aqueous solution was 6.0 equivalents with respect to the mole number of DOPA in the DOPA aqueous solution.

Thereafter, while the DOPA aqueous solution was agitated in the reaction tank, the potassium hexacyanoferrate (III) aqueous solution in the oxidizing agent tank was dropped into the reaction tank for 10 minutes and aged for four hours from the start of dropping so that oxidation-reduction reaction of DOPA and potassium hexacyanoferrate (III) was caused to occur to generate DHI, thereby obtaining an aqueous first solution. During this process, the liquid temperature of the reaction solution in the reaction tank was maintained at 35° C.

Subsequently, while the first solution in the reaction tank was agitated, a phosphoric acid aqueous solution having a dissolved oxygen concentration of 1.0 mg/L or less and a concentration of 10% by mass was added as a pH adjuster to the reaction tank so that the pH was adjusted to 4.7. A part of the obtained first solution was taken out, and the content of DHI in this part was measured by HPLC, thereby calculating a molar quantity of DHI in the first solution.

Then, the first solution in the reaction tank reaction tank was caused to circulate in the circulation pipe and was filtered by a filter, thereby removing a water-insoluble by-product. The number of passes for the first solution in the circulation pipe was five.

—Refining Process (Step 2)—

A part of the first solution from which the water-insoluble by-product was removed by filtration was taken out and transferred to a screw tube No. 7. Then, the first solution in the screw tube was supplemented with 50% by volume of ethyl acetate with respect to the first solution as an extraction solvent, and the screw tube was shaken by hand so that the mixture was sufficiently agitated, thereby obtaining an oleaginous second solution in which DHI was extracted in ethyl acetate as the extraction solvent. Thereafter, the agitation was stopped, and phases of the aqueous first solution and the oleaginous second solution were separated. Subsequently, only the upper-layer second solution was collected by using a pipet, a part of the obtained second solution was taken out, the content of DHI in this part was measured by HPLC, and a molar quantity of DHI in the collected second solution was calculated.

Second Example

—Reaction Process (Step 1)—

In a second example, first, a nitrogen gas was continuously supplied to a reaction tank having a capacity of 500 mL, and water whose dissolved oxygen concentration had been adjusted to 1.0 mg/L or less by blowing a nitrogen gas was poured into the reaction tank. While water was agitated in the reaction tank, DOPA was placed and dissolved in the reaction tank, thereby preparing 348 mL of a DOPA aqueous solution (DOPAs solution) having a concentration of 0.33% by mass. At this time, the liquid temperature of the DOPA aqueous solution was adjusted to 35° C.

In addition, potassium hexacyanoferrate(III) of an oxidizing agent and potassium hydrogencarbonate of a base agent were placed and dissolved in ion-exchanged water, thereby preparing 41 mL of a potassium hexacyanoferrate(III) aqueous solution (oxidizing agent solution) having a concentration of 16.8% by mass. The content of potassium hexacyanoferrate(III) in this potassium hexacyanoferrate(III) aqueous solution was 4.0 equivalents with respect to the mole number of DOPA in the DOPA aqueous solution. The content of potassium hydrogencarbonate of the base agent in the potassium hexacyanoferrate(III) aqueous solution was 6.0 equivalents with respect to the mole number of DOPA in the DOPA aqueous solution.

Thereafter, while the DOPA aqueous solution was agitated in the reaction tank, the potassium hexacyanoferrate (III) aqueous solution was dropped into the reaction tank for five minutes and aged for four hours from the start of dropping so that oxidation-reduction reaction of DOPA and potassium hexacyanoferrate(III) was caused to occur to generate DHI, thereby obtaining an aqueous first solution. During this process, the liquid temperature of the reaction solution in the reaction tank reaction was maintained at 35° C.

Subsequently, while the first solution in the reaction tank was agitated, a phosphoric acid aqueous solution having a dissolved oxygen concentration of 1.0 mg/L or less and a concentration of 10% by mass was added as a pH adjuster to the reaction tank so that the pH was adjusted to 4.7. A part of the obtained first solution was taken out, and the content of DHI in this part was measured by HPLC, thereby calculating a molar quantity of DHI in the first solution.

Then, a part of the first solution in the reaction tank was taken out and filtered with a filter medium having an aperture of 2.0 μm, thereby removing a water-insoluble by-product.

—Refining Process (Step 2)—

The first solution from which the water-insoluble by-product was removed by filtration was transferred to a screw tube No. 7. Then, the first solution in the screw tube was supplemented with 50% by volume of ethyl acetate with respect to the first solution as an extraction solvent, and the screw tube was shaken by hand so that the mixture was sufficiently agitated, thereby obtaining an oleaginous second solution in which DHI was extracted in ethyl acetate as the extraction solvent. Thereafter, the agitation was stopped, and phases of the aqueous first solution and the oleaginous second solution were separated. Subsequently, only the upper-layer second solution was collected by using a pipet, a part of the obtained second solution was taken out, the content of DHI in this part was measured by HPLC, and a molar quantity of DHI in the collected second solution was calculated.

Third Example

In a third example, an operation similar to that in the second example was performed except for using a filter medium having an aperture of 5.0 μm.

Fourth Example

In a fourth example, an operation similar to that of the second example was performed except for removing a water-insoluble by-product by performing centrifugal separation of the first solution. The centrifugal separation was performed in such a manner that 7 mL of the first solution in the reaction tank was placed in a centrifuge tube having a capacity of 15 mL, and centrifugal separation was performed at a rotation speed of 5000 rpm for a rotation time of two minutes.

Comparative Example

In a comparative example, an operation similar to that of the second example except for not removing a water-insoluble by-product through filtration.

(Test Method and Result)

An extraction yield was obtained for the oleaginous second solution obtained in each of the first through fourth examples and the comparative example. The extraction yield was calculated as a percentage of the molar quantity contained in DHI in the second solution with respect to the molar quantity contained in DHI in the first solution.

A phase separation rate was also obtained for each of the first through fourth examples and the comparative example. The phase separation rate was obtained by dividing a liquid height when ethyl acetate as an extraction solvent was added to the first solution by a time necessary for phase separation from stop of agitation by shaking the screw tube.

Table 1 shows the results. Table 1 shows that the first through fourth examples in which the water-insoluble by-product was removed show higher extraction yields and higher phase separation rates than those in the comparative example in which the water-insoluble by-product was not removed.

INDUSTRIAL APPLICABILITY

The present invention is useful for a technical field of a method for producing dihydroxyindoles.

DESCRIPTION OF REFERENCE CHARACTERS

D DOPAs solution
O oxidizing agent solution
L1 first solution
L1 second solution
L3 third solution
W water
10 reaction apparatus
11 reaction tank
12 oxidizing agent tank
13 oxidizing agent supply pipe
14 discharge pipe
151, 152 agitator
151a, 152a agitating impeller
16 jacket
171, 172 filter
17a filter medium
181 circulation pipe

TABLE 1

| | | | Example | | | | Comparative |
|---|---|---|---|---|---|---|---|
| | | | 1 | 2 | 3 | 4 | Example |
| DOPAs solution | DOPAs type | | DOPA | DOPA | DOPA | DOPA | DOPA |
| | concentration (% by mass) | | 0.33 | 0.33 | 0.33 | 0.33 | 0.33 |
| oxidizing agent solution | oxidizing agent type | | $K_3[Fe(CN)_6]$ | $K_3[Fe(CN)_6]$ | $K_3[Fe(CN)_6]$ | $K_3[Fe(CN)_6]$ | $K_3[Fe(CN)_6]$ |
| | DOPAs equivalent (eq.) | | 4.0 | 4.0 | 4.0 | 4.0 | 4.0 |
| | base agent type | | $KHCO_3$ | $KHCO_3$ | $KHCO_3$ | $KHCO_3$ | $KHCO_3$ |
| | DOPAs equivalent (eq.) | | 6.0 | 6.0 | 6.0 | 6.0 | 6.0 |
| | water-insoluble by-product removal | | done | done | done | done | no |
| | water-insoluble by-product method | | filtration | filtration | filtration | centrifugal separation | — |
| removal condition | filtration | filter aperture (μm) | 1.2 | 2.0 | 5.0 | — | — |
| | centrifugal separation | rotation number (rpm) | — | — | — | 5000 | — |
| | | rotation time (min.) | — | — | — | 2 | — |
| extraction solvent | extraction solvent type | | Ethyl acetate | Ethyl acetate | Ethy acetate | Ethyl acetate | Ethyl acetate |
| | LogP | | 0.73 | 0.73 | 0.73 | 0.73 | 0.73 |
| extraction yield (mol%) | | | 85 | 65 | 29 | 28 | 20 |
| phase separation rate (cm/sec) | | | 0.28 | 0.069 | 0.054 | 0.044 | 0.042 |
| purity (%) | | | >95 | >95 | >95 | >95 | >95 |

182 inter-tank coupling pipe
19 filtrate tank

The invention claimed is:

1. A method for producing dihydroxyindoles, comprising:
    a step 1 of obtaining an aqueous first solution including dihydroxyindoles obtained by causing at least a material selected from the group consisting of 3-(3,4-dihydroxyphenyl)alanine and a derivative of 3-(3,4-dihydroxyphenyl)alanine to react with an oxidizing agent; and
    a step 2 of obtaining an oleaginous second solution in which the dihydroxyindoles are extracted in an extraction solvent by mixing the first solution obtained in the step 1 with the extraction solvent, wherein
    before the first solution obtained in the step 1 is mixed with the extraction solvent in the step 2, a water-insoluble by-product is removed from the first solution.

2. The method according to claim 1, wherein the water-insoluble by-product is removed by filtration.

3. The method according to claim 2, wherein the filtration uses a filter medium having an aperture of 5.0 µm or less.

4. The method according to claim 2, wherein the filtration uses a filter medium having an aperture of 1.5 µm or less.

5. The method described in claim 2, wherein the filtration uses a filter medium having an aperture of 0.1 µm or more.

6. The method described in claim 2, wherein the filtration is formed by causing the first solution to circulate in a circulation pipe provided with a filter including the filter medium.

7. The method described in claim 6, wherein the number of circulations of the first solution in the circulation pipe is twice or more and 10 times or less.

8. The method described in claim 2, wherein the filtration is performed through one-pass filtration by distributing the first solution in a pipe provided with a filter including the filter medium.

9. The method according to claim 1, wherein in the step 1, an aqueous solution or an aqueous suspension including 0.2% by mass or more of at least a material selected from the group consisting of the 3-(3,4-dihydroxyphenyl)alanine and a derivative of the 3-(3,4-dihydroxyphenyl)alanine is mixed with an aqueous solution or an aqueous suspension of the oxidizing agent.

10. The method according to claim 1, wherein in the step 1, an aqueous solution or an aqueous suspension including 0.3% by mass or more of at least a material selected from the group consisting of the 3-(3,4-dihydroxyphenyl)alanine and a derivative of the 3-(3,4-dihydroxyphenyl)alanine is mixed with an aqueous solution or an aqueous suspension of the oxidizing agent.

11. The method according to claim 9, wherein the oxidizing agent includes alkali metal salt of hexacyanoferrate (III) acid.

12. The method according to claim 9, wherein an aqueous solution or an aqueous suspension of the oxidizing agent includes a base agent.

13. The method according to claim 12, wherein the base agent includes alkali metal salt of hydrogencarbonate ions.

14. The method according to claim 12, wherein a content of the base agent with respect to a mole number of the 3-(3,4-dihydroxyphenyl)alanine and the derivative of 3-(3,4-dihydroxyphenyl)alanine is 3.9 equivalents or more and 9.0 equivalents or less.

15. The method according to claim 1, wherein the extraction solvent includes an organic solvent whose octanol/water distribution coefficient is 0 or more and 4.0 or less.

16. The method according to claim 15, wherein the extraction solvent includes ethyl acetate.

* * * * *